(12) United States Patent
Luk et al.

(10) Patent No.: US 8,940,911 B2
(45) Date of Patent: Jan. 27, 2015

(54) SQUARYLATED LACTONES INHIBITORS FOR BACTERIAL BIOFILM FORMATION

(71) Applicants: Yan-Yeung Luk, Jamesville, NY (US); Sri Kamesh Narasimhan, Syracuse, NY (US); Eric Falcone, Syracuse, NY (US)

(72) Inventors: Yan-Yeung Luk, Jamesville, NY (US); Sri Kamesh Narasimhan, Syracuse, NY (US); Eric Falcone, Syracuse, NY (US)

(73) Assignee: Syracuse University, Syracuse, NY (US)

(*) Notice: Subject to any disclaimer, the term of this patent is extended or adjusted under 35 U.S.C. 154(b) by 0 days.

(21) Appl. No.: 13/957,038

(22) Filed: Aug. 1, 2013

(65) Prior Publication Data

US 2014/0039195 A1 Feb. 6, 2014

Related U.S. Application Data

(60) Provisional application No. 61/678,357, filed on Aug. 1, 2012.

(51) Int. Cl.
| C07D 409/12 | (2006.01) |
| C07D 307/32 | (2006.01) |
| C07D 307/20 | (2006.01) |
| C07D 405/12 | (2006.01) |
| A01N 43/16 | (2006.01) |
| A61K 31/35 | (2006.01) |

(52) U.S. Cl.
CPC ............ *C07D 307/20* (2013.01); *C07D 409/12* (2013.01); *C07D 405/12* (2013.01); *C07D 307/32* (2013.01)
USPC .......... 549/321; 549/60; 548/356.5; 548/517; 546/284.7; 514/460

(58) Field of Classification Search
USPC ........................................ 514/460; 546/284.7
See application file for complete search history.

(56) References Cited

U.S. PATENT DOCUMENTS 7,642,285 B2 * 1/2010 Blackwell et al. ............ 514/471

OTHER PUBLICATIONS

Marin; Bioorganic & Medicinal Chemistry Letters 17 (2007) 1549-1552.*

* cited by examiner

*Primary Examiner* — John Mabry
*Assistant Examiner* — Daniel Carcanague
(74) *Attorney, Agent, or Firm* — David L. Nocilly; George R. McGuire; Bond Schoeneck & King, PLLC

(57) ABSTRACT

A library of unnatural squarylated homoserine lactones (SHLs) and squarylated lactones that bear potential to modulate biofilm formation in Gram negative bacteria. At low concentrations (~200 μM), these small molecules inhibit biofilm formation of *E. coli*. Moreover, these compounds are not toxic up to 300 μM and do not significantly attenuate *E. coli* growth. The SHLs have potential to disperse established biofilm and demonstrate an enhanced reduction (~50%) of the maximum biofilm thickness by use of SHLs during biofilm growth.

7 Claims, 18 Drawing Sheets

Other relevant structures

Structures for background information

SQUARYLATED LACTONES INHIBITORS FOR BACTERIAL BIOFILM FORMATION

BACKGROUND OF THE INVENTION

1. Field of the Invention

The present invention relates to biofilm inhibitors and, more particularly, squarylated lactones for inhibiting quorum sensing.

2. Description of the Related Art

The term quorum sensing (QS) refers to the ability of a microorganism to sense and monitor the presence of other microbes by producing and responding to signal molecules called autoinducers (also AI). QS regulates microbial population levels and is a critical determinant of biological processes like biofilm formation, luminescence or pathogenesis that is crucial for the microbial growth and survival. This cell-to-cell communication is carried out by signals such as N-acyl-L-homoserine lactones (AHLs) that bind to their cognate receptors when critical cell density is reached leading to optimal physiological and communal response.

QS generally govern multi-cellular behavior like bioluminescence, secretion of virulence factors, biofilm formation, sporulation, conjugation and pigment production. Initially, QS was considered to be a mechanism by which microbial cells count each other. But, recent evidence suggests that QS process can be induced by even a few cells confined to a very small volume. Generally, each species of bacteria tend to produce and detect signaling molecules that are responsible for their multi-cellular behavior. Among prokaryotes, the Gram negative bacteria use, extensively, signal molecules that have acyl homoserine lactones (also called autoinducer 1; AHLs) moieties in their structure. These signals effectively enter the cells, upon quorum, via diffusion and interact with their corresponding intracellular effectors. Upon reaching threshold concentrations these small molecules are detected by the cognate cytoplasmic LuxR-type proteins, which bind their corresponding autoinducers, and further bind to DNA to activate transcription of preferred target genes that may produce biofilm or virulence. The specificity of LuxR-AHL interactions is determined by the ability of the AHL signal's acyl chain to fit the hydrophobic binding pocket of the LuxR protein. Apart from the AHLs and the peptide-based signaling molecules, interspecies communication is facilitated by molecules called AI-2 (autoinducer 2).

The AI-2 is a generic name for a family of signal molecules having a basic furanosyl borate diester structure. All these molecules have a common precursor, 4,5-dihydroxy-2,3-pentanedione (DPD) that is generated by the LuxS enzyme. QS in *E. coli* has evoked significant interest leading to the discovery of different intercellular signaling pathways including those mediated by LuxR homolog SdiA, a LuxS/AI-2 system consisting of proteins LsrR and LsrK, an unknown AI-3 system and an indole mediated signaling system. There is lack of clarity regarding the QS apparatus in *E. coli* due to the incomplete availability of QS components. Moreover, some of the putative QS signals are intertwined with metabolism and it is not entirely possible to dissect the role of QS signals in both these processes. The AI-2 signal is considered to be responsible for interspecies communication in both Gram positive and Gram negative bacteria. For instance, *E. coli* detects and responds to AI-2 secreted by *V. harveyi* to assess changes in its cell population. DPD rearranges spontaneously into a family of AI-2 signals that have been attributed to cause formations of biofilms in *E. coli*.

Biofilms constitute a community of microorganisms in which the cells are attached to the surface by means of a self-produced matrix called extracellular polymeric substance (EPS) or "slime". The polymeric matrix is derived of proteins, nucleic acids and polysaccharides. Biofilms can form on biotic or abiotic surfaces and are prevalent in nature or in an industrial and hospital setting. The microbial cells existing in a planktonic form or in biofilms are found to vary physiologically and display differential genetic expressions.

Managing biofilms is currently a major area of interest as biofilms have huge implications in the health care industry. According to the United States National Institutes of Health, about 80% of chronic infections are biofilm related. The biofilm generally includes several bacterial species and as it gets thicker, the matrix assumes a complex structure and becomes impenetrable to the antibiotics. Biofilms routinely foul up medical instruments like catheters and implants, occur as dental plaques, lead to chronic ailments and persistent lung infections in cystic fibrosis patients that are mediated by *Pseudomonas aeruginosa* and are suspects in variety of diseases like prostatitis, endocarditis, and conjunctivitis. Researchers are just beginning to understand that bacterial cells in biofilms are 10-1000 times more resistant to antibiotics than in their planktonic counterparts. Destroying the bacterial cells in biofilms in exceedingly difficult due to the nature of the matrix and also because the bacterial cell behavior is changed. Apparently, bacterial cells in a biofilm have lower metabolism, are relatively quiescent and are rarely dividing. Most anti-bacterials unfortunately target dividing cells and are aimed at metabolism, DNA or protein synthesis.

Due to the considerable medical problems posed by biofilms there is a continued need and desire to develop newer antimicrobial tools that target not merely biofilms but the processes that lead to the formation of biofilms. Emergence of newer multi-drug resistant strains of microbes has made the development of novel approaches and tools to treat microbial diseases a top priority. Using chemical methods, the first approach could target the QS process itself causing quenching of cell-to-cell communication leading to prevention of multicellular behavior like biofilm formation and virulence. For instance, developing autoinducer analogs that block the LuxR, LuxS or LuxI-type proteins and inhibit their activities would be of great interest. The second approach could entail the use of enzymes to enable degradation of AHLs. For instance, lactonase AiiA from *A. tumefaciens* degrades AHLs and the lactonase AiiA from *Bacillus* species can hydrolyze the AHLs lactone ring to acyl homoserine, an ineffective QS signal, and prevent *E. caratovora* to cause soft rot disease in plants. The third approach could potentially target the AHL biosynthetic pathway, encouraging interruption in AHL production by use of synthetic analogs of AHL precursors. Recently antibodies and natural products have been used to break down QS and biofilm development in Gram-negative bacteria. On the other hand, with surfaces the incentive is to develop novel bio-inert surface chemistry tools that would inhibit the cell adhesion process itself thereby eliminating any possibility of biofilm formation.

Over the past 20 years or so, a significant amount of research has been directed towards the design and synthesis of ligands that disrupt AHL binding to its cognate receptors and inhibit QS. A variety of non-natural systems including synthetic mimics of marine natural products and modified AHLs have been developed primarily to modulate QS in microbial populations, but there still exists a scarcity of non-toxic inhibitors of QS and biofilm formation. New design and synthetic strategies are clearly needed to expand the current set of quorum-sensing modulators in Gram negative bacteria. Designing new quorum sensing modulators has been an increasing challenge because the few synthetically developed
} antagonists and agonists of quorum sensing have diverse structures and their mechanism of action is unclear. Moreover, as multiple microbial species generally co-exist together there is a significant motivation to develop chemical signal entities that can either selectively target or display broad-range activity against multiple AHL-receptor proteins that are available. At this juncture, it is interesting to note that the homology of the putative binding sites of the ~50 well-known AHL-receptor proteins (70-80%) suggests that if non-natural mimics of AHL target these sites then both selective and broad-spectrum molecules could be developed.

BRIEF SUMMARY OF THE INVENTION

It is therefore a principal object and advantage of the present invention to provide controlled manipulation of QS for beneficent effects such as reduced microbial population, thereby leading to a lower pathogenicity or an increased microbial density that has an application towards bioremediation.

It is an additional object and advantage of the present invention to provide the design and synthesis of a library of squarylated homoserine lactones that display an ability to modulate quorum sensing process at sub-millimolar concentrations resulting in inhibition and dispersal of bacterial biofilm.

In accordance with the foregoing objects and advantages, the present invention provides the design and efficient synthesis, in 2 steps, of a library of unnatural squarylated homoserine lactones (SHLs) and squarylated lactones that bear potential to modulate biofilm formation in Gram negative bacteria. At low concentrations (~200 µM), these small molecules inhibit biofilm formation of $E.$ $coli.$ Moreover, these compounds are not toxic up to 300 µM and do not significantly attenuate $E.$ $coli$ growth. The SHLs, more significantly, seem to have potential to disperse established biofilm. Furthermore, confocal microscopy studies validate an enhanced reduction (~50%) of the maximum biofilm thickness by use of SHLs during biofilm growth.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 3:
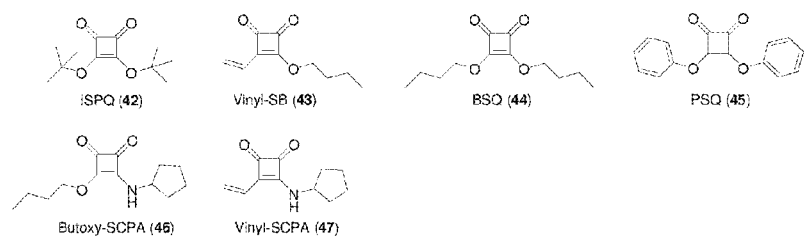
Figure 3:
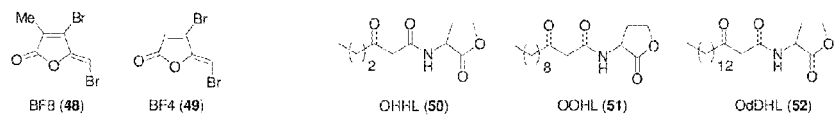

FIG. 3 is a series of structures of other relevant and background compounds. Compounds 45 and 48 were synthesized previously. Squarylated esters 42 and 43 and the naturally occurring auto inducers 50-52 were purchased commercially.

Note that (a) N—C bonds in compounds 4 and 5 is racemic (b) 2° amide-like E and Z rotamers exist in 1-3 and 6-41, 46, and 47 (c) vinyl group is syn/anti with respect to the endocyclic double bond in 3, 4, 5, 43 and 47.

Figure 3A:
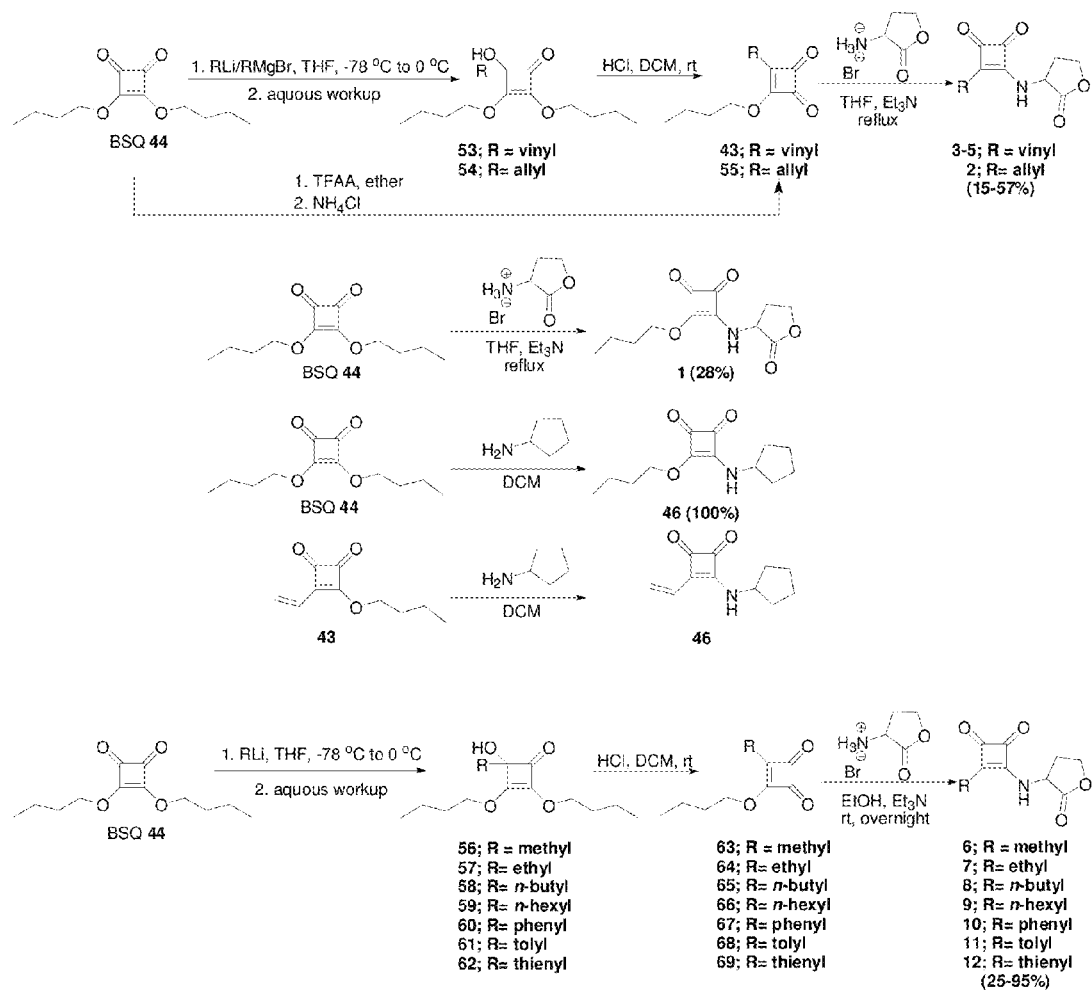

FIG. 3A is the synthesis of squarylated homoserine lactones (SHLs), squarylated esters and squarylated amides according to the present invention.

Figure 4:
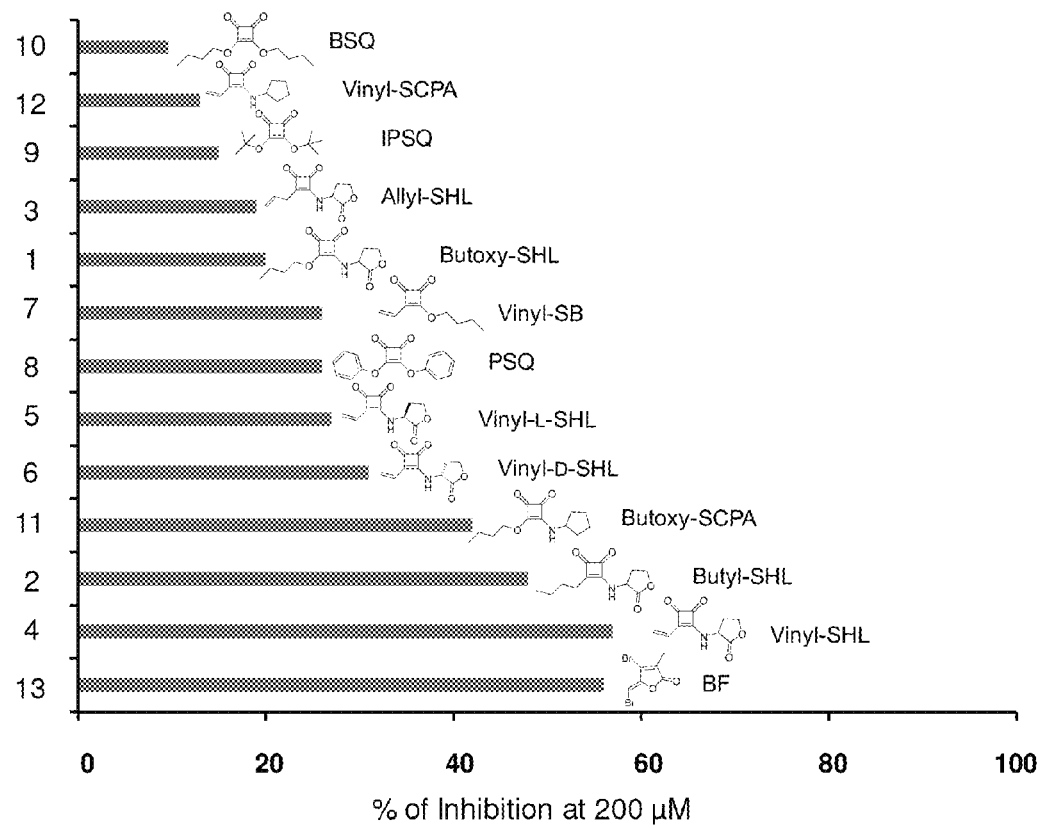

FIG. 4 is a chart of biofilm inhibition activity by selected squarylated homoserine lactone (SHL) 1-5, 8, squarylated esters 42-45, squarylated amides 46-47 and brominated furanone 48 against $E.$ $coli$ RP437 at 200 µM.

Figure 5:
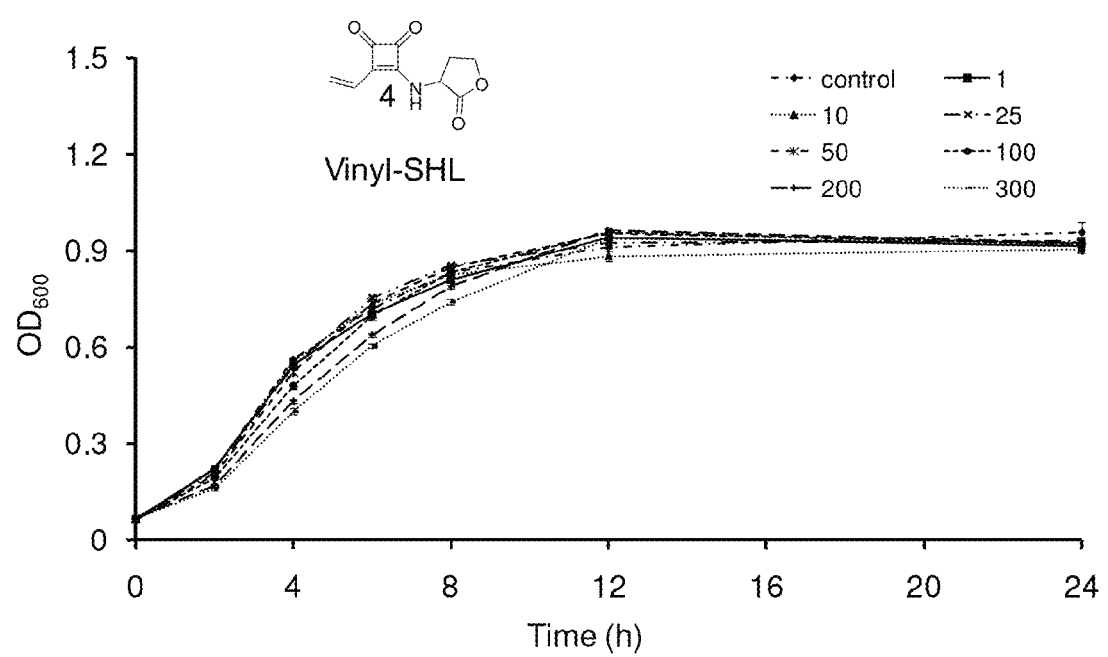

FIG. 5 is a graph of growth curves of $E.$ $coli$ RP437 in the presence of vinyl-SHL 3 at various concentrations.

Figure 6:
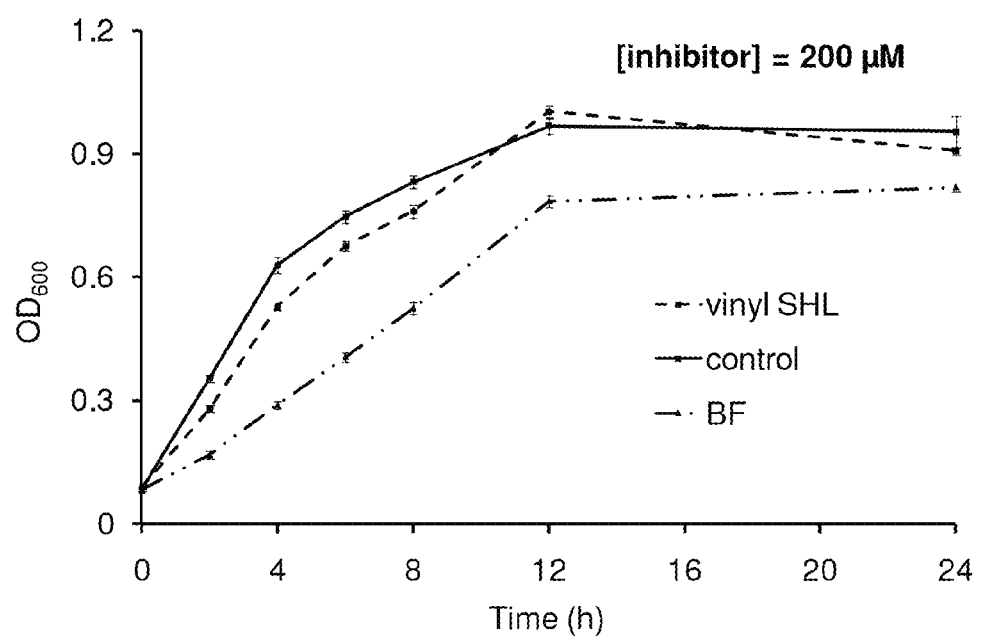

FIG. 6 is a graph of growth curves of $E.$ $coli$ RP437 in the presence of vinyl-SHL 3 and BF8 48 at 200 µM.

Figure 6A:
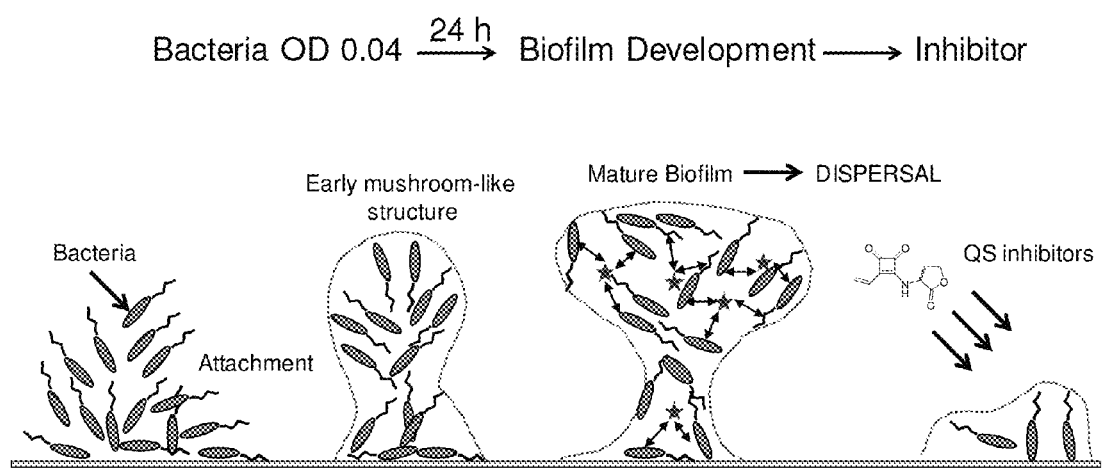

FIG. 6A is a scheme of squarylated homoserine lactone mediated dispersal of biofilms formed by $E.$ $coli$ RP437.

Figure 7:
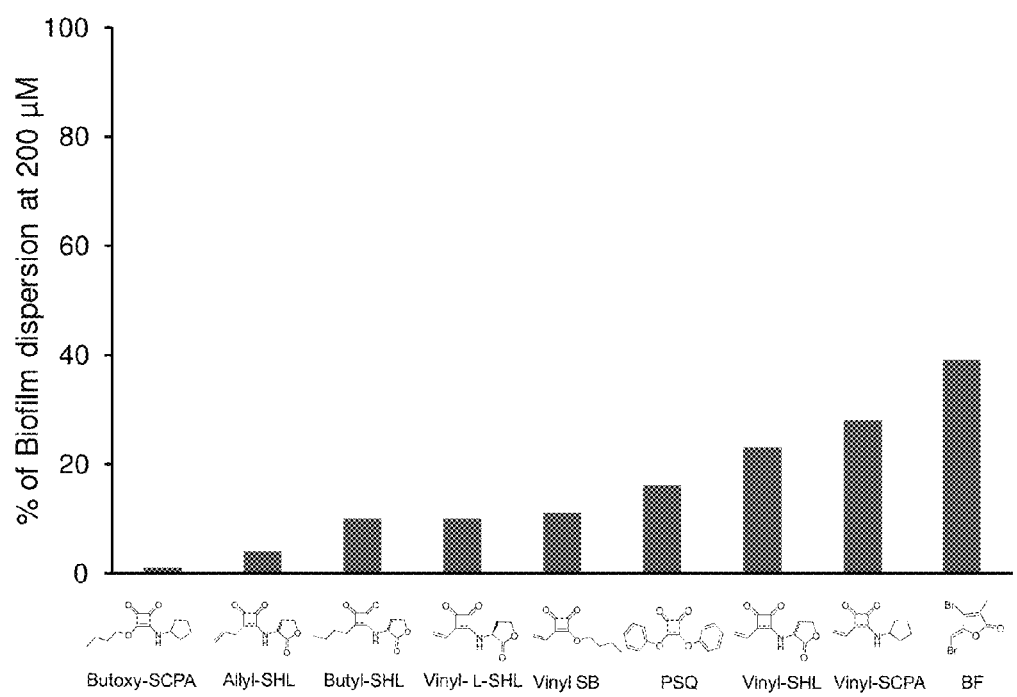

FIG. 7 is a chart of the dispersion of $E.$ $coli$ RP437 biofilms in the presence of SHLs 2-4, 8, 43, 46-47 and BF8 48 at 200 µM.

Figure 8:
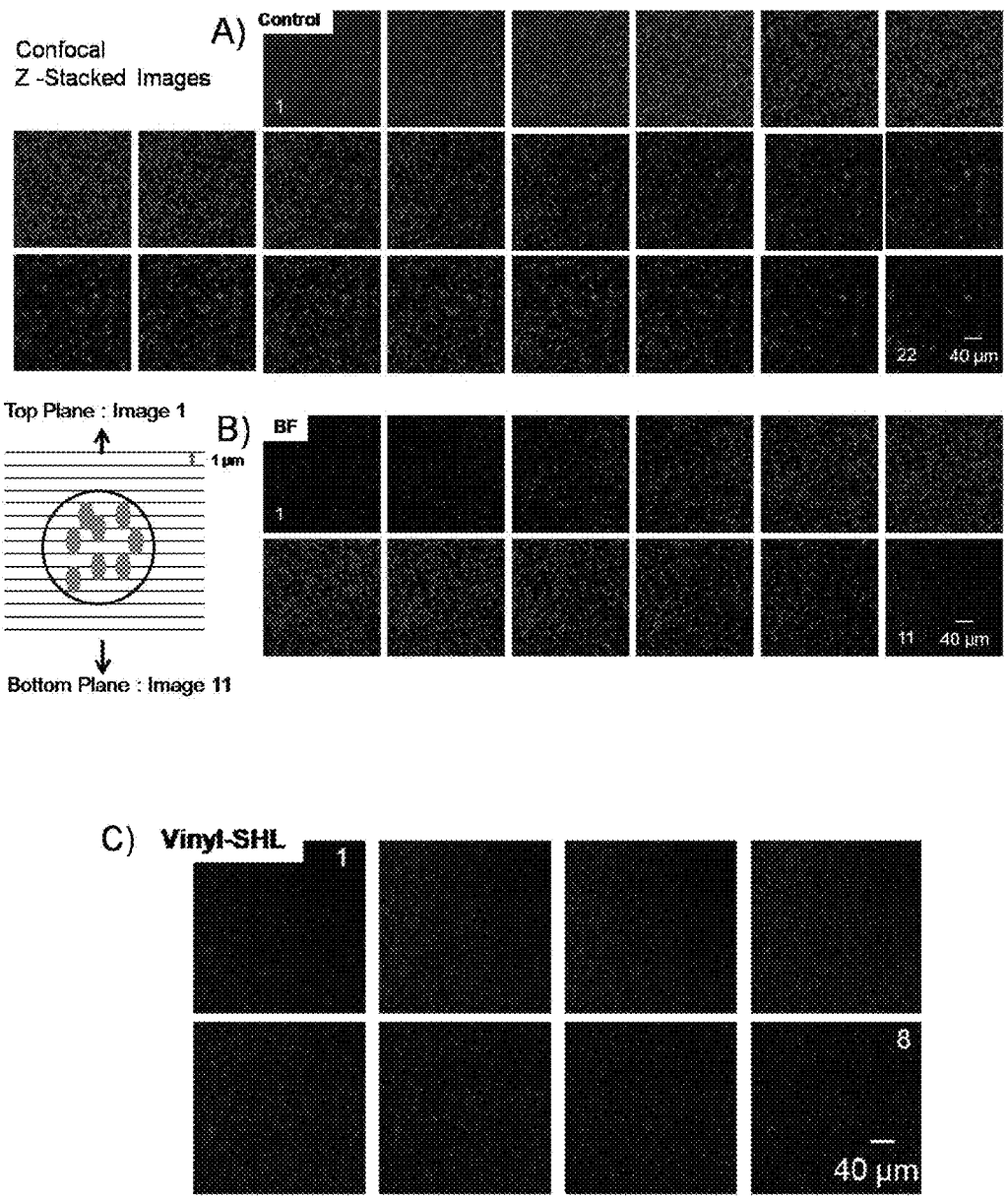

FIG. 8 is a series of confocal images of biofilms formed by DsRed-express-labeled $E.$ $coli$ RP437 in the absence of inhibitor (A); in the presence of 200 µM BF8 48 (B), and 200 µM vinyl-SHL 3 (C).

Figure 9:
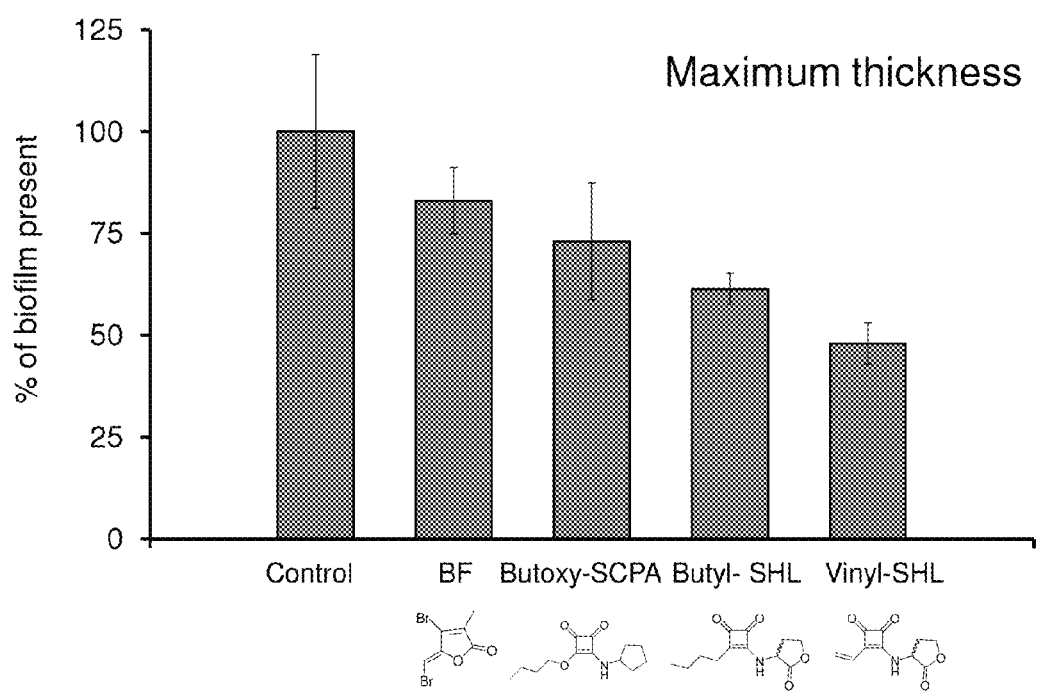

FIG. 9 is a chart of the effects of compounds 3, 8, 46, and 48 on the maximum biofilm thickness measured by confocal fluorescent signal. The structure of each compound is shown below the chart.

Figure 10:
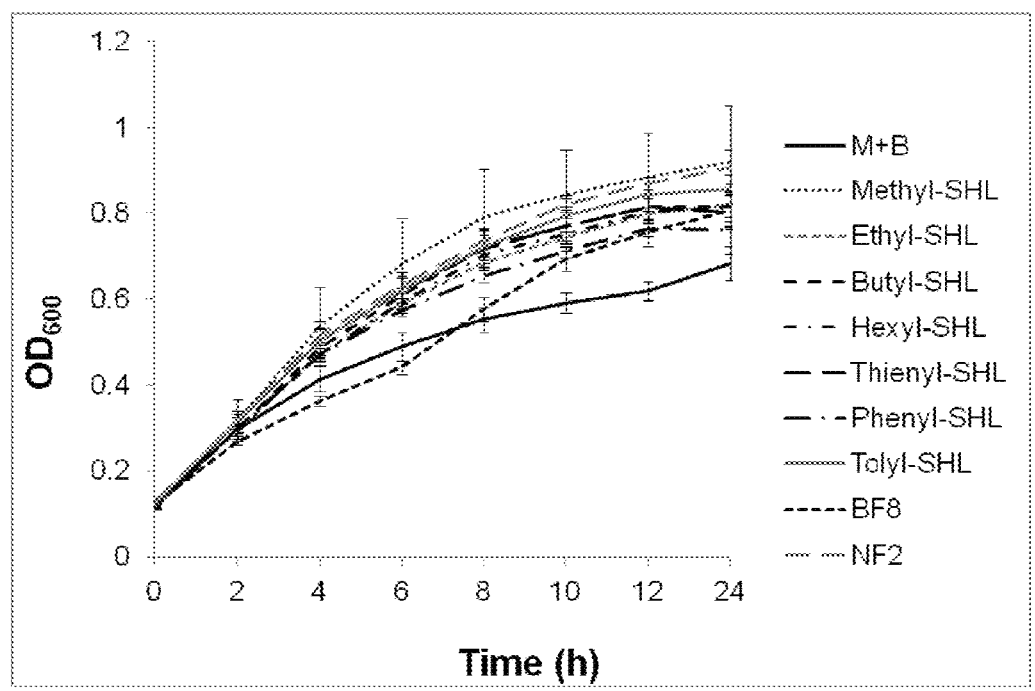

FIG. 10 is a graph of growth curve of $E.$ $coli$ RP437 in the absence and presence of 200 µM SHL 6-12 and brominated furanone 48.

Figure 11:
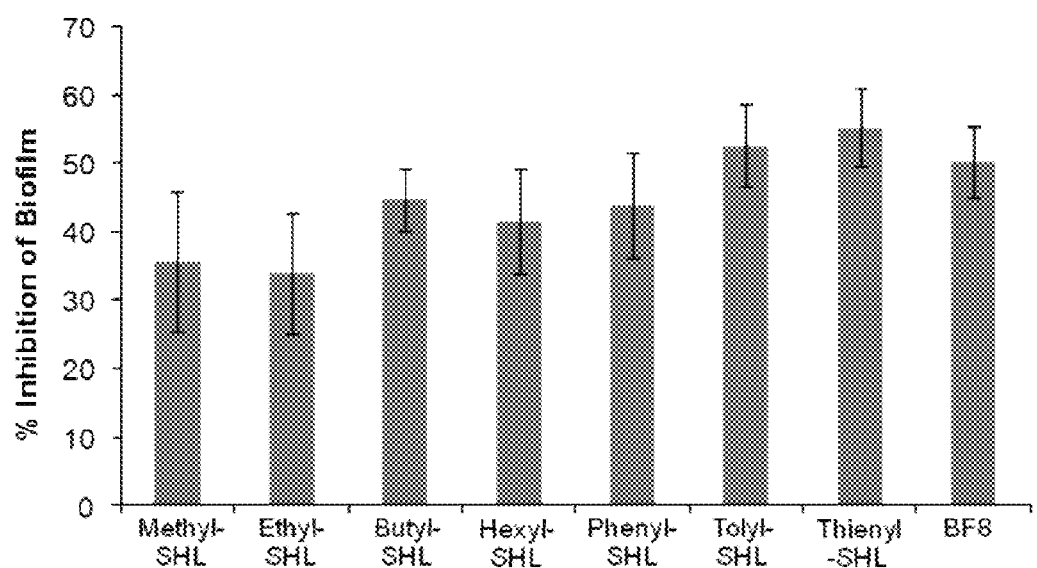

FIG. 11 is a chart of biofilm inhibition activity of squarylated homoserine lactone (SHL) 6-12 and brominated furanone 48 against $E.$ $coli$ RP437 at 200 µM.

Figure 12:
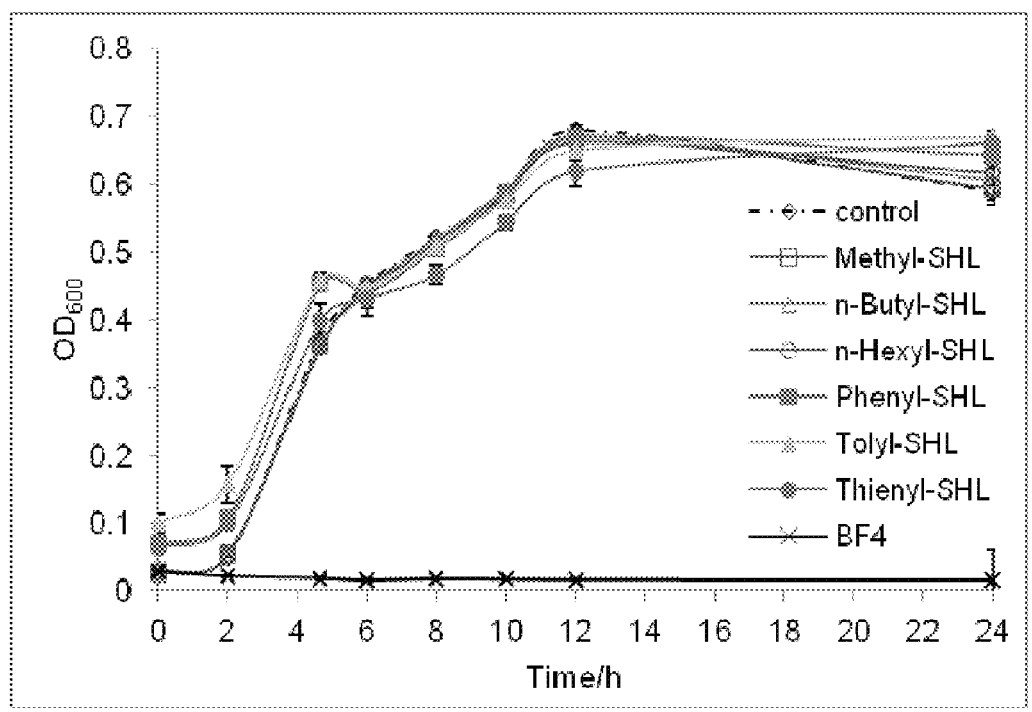

FIG. 12 is a graph of growth curve of $P.$ $aeruginosa$ PAO1 in the absence and presence of 300 µM SHL 6-12 and brominated furanone 48.

Figure 13:
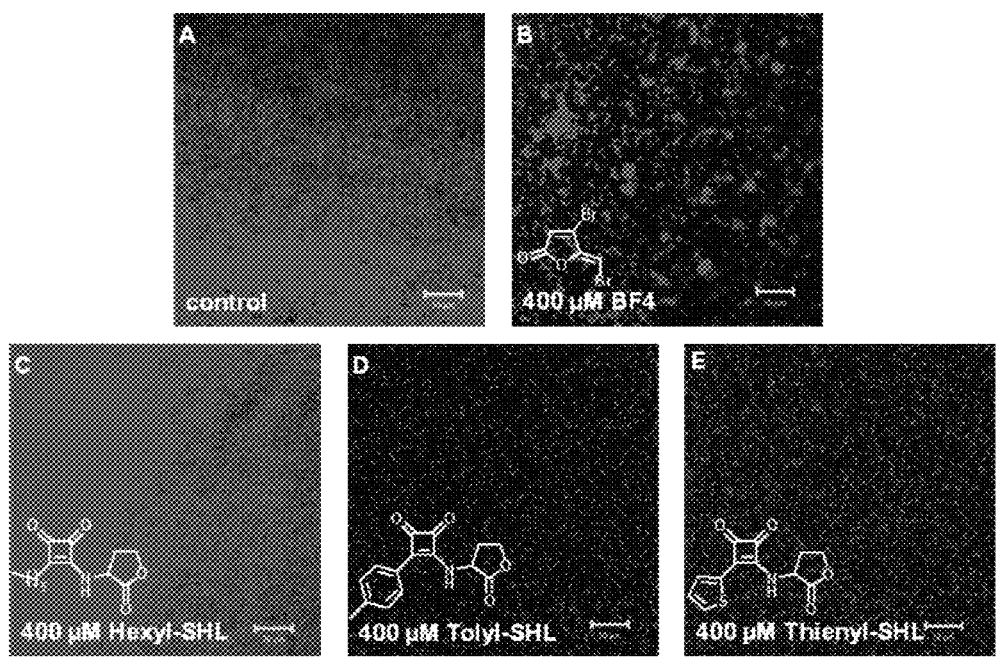

FIG. 13 is a series of representative confocal laser scanning microscopy images of biofilm formation by $P.$ $aeruginosa$ PAO1-GFP/pSMC2 in the absence of inhibitor (A); and in the presence of 400 µM BF4 49 (B); 400 µM hexyl-SHL 9 (C); 400 µM tolyl-SHL 11 (D); and 400 µM thienyl-SHL 12 (E).

Figure 14:
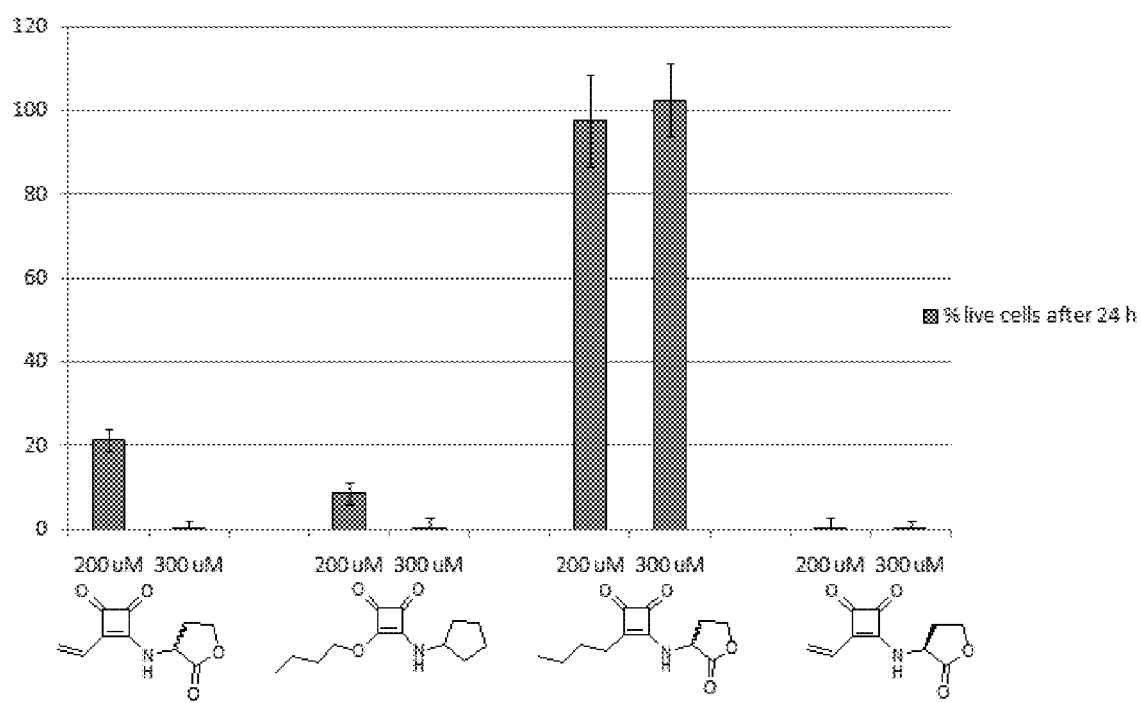

FIG. 14 is a graph of quantification of biofilm formation by $P.$ $aeruginosa$ PAO1-GFP/pSMC2 in the absence and presence of 400 µM SHLs 9, 11 and 12. Biomass, mean thickness, and surface area are quantified from fluorescence image using COMSTAT software. Z-Stack images from at least four different locations were used. Values are normalized by that of the brominated furanone-free control.

Figure 15:
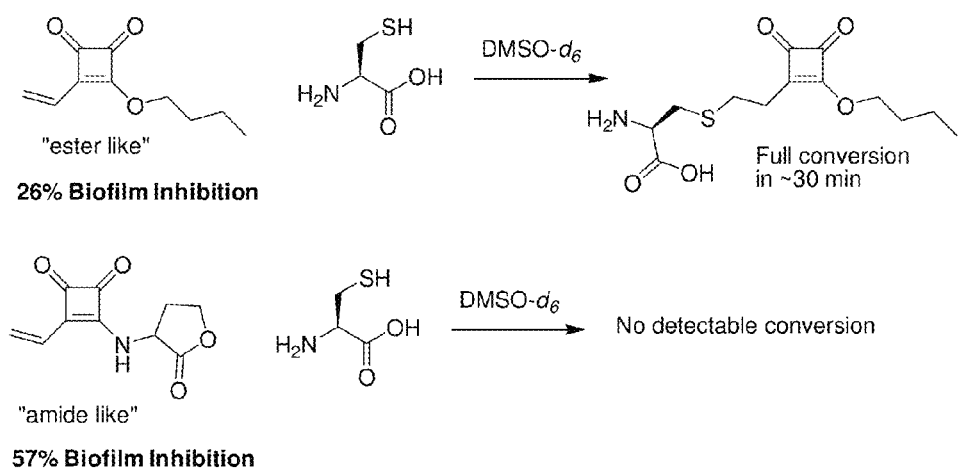

FIG. 15 is a chart of the effect of key potent biofilm inhibitors 3, 4, 8, and 46 on the growth of human neuroblastoma cancer cells after 24 h. The structure of each compound is shown below the chart.

Figure 16:
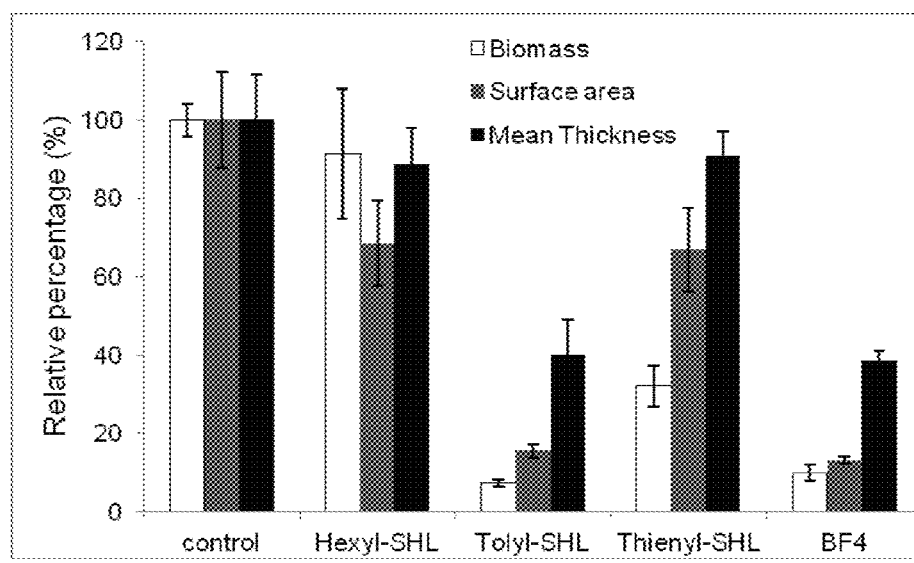

FIG. 16 is a scheme showing that the chemical reactivity of SHLs does not correlate with their inhibition activity against $E.$ $coli$ biofilms.

DETAILED DESCRIPTION OF THE INVENTION

Design and Synthesis of Squarylated Homoserine Lactones (SHLs)

Clearly AHLs possess tremendous capabilities to modulate quorum sensing phenomenon across the breadth of the Gram negative bacteria. AHLs hold the key structural pre-requisites required for developing the necessary tools to control bacterial cell-to-cell communication and biofilm formation. The AHLs are made of a linear long aliphatic chain that offer a significant array of folded structures, wherein multiple minimum energy conformations can be adopted, leading to presumably weaker receptor binding. AHLs lack of rigid backbone permits non-regulated random rotation affording infinite conformational ensembles.

Figure 1:
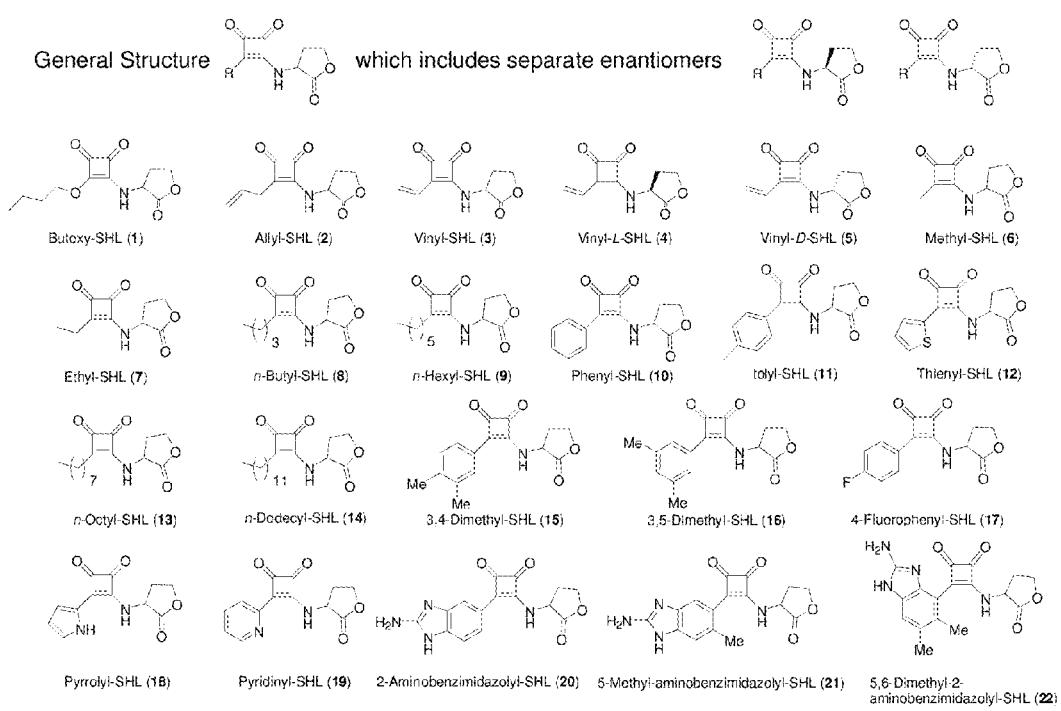
FIG. 1 is a general library of the first generation of squarylated homoserine lactones as synthetic mimics of autoinducer.

The present invention is based on an introduction of a cyclic constraint in the AHL backbone, thereby, reducing the number of non-random well-folded states. The enhanced rigidity is believed to permit an increased receptor binding and expected to offset the excessive entropic cost of cyclization. To serve this purpose, the present invention introduces the squarate moiety to provide an important structural element towards the development of a new class of synthetic AI-1 mimics that present as squarylated homoserine lactones (SHLs), as seen in FIG. 1. The squarate molecule was selected for the following reasons; the squarate molecule offers a four-membered centrally constrained ring system; the squarate moiety does not contain native amide bonds, and thus has a low propensity to be degraded by enzymes; the squarate group being rigid allows the SHLs to exist in only four possible conformations due to the extensive π conjugation. Finally, the squarate enhances the electrophilicity of SHLs, a necessary design prerequisite that would encourage putative Michael-type additions to occur on the SHLs presumably during their active site binding interactions.

To gain an understanding of the activity profile of this unique class of molecules, the present invention involves the synthesis of a library of analogues based upon the squarylated backbone. The intention was to generate SHLs rapidly using relatively short reaction sequences to allow systematic screening for their anti-biofilm properties. The present invention thus involved synthesis of a series of squarylated lactones, esters and amides, using a rapid, two-step reaction. Subjecting the commercially available 3,4-dibutoxy-cyclobut-3-ene-1,2-dione (BSQ) 44 with suitable Grignard/organolithium reagents promoted a 1,2-addition reaction on the carbonyl group leading to the oxyanion formation. Further treatment with use of trifluoroacetic anhydride trapped the oxyanion as a trifluoroacetate ester and its subsequent hydrolysis afforded the squarylated ester intermediate, which on treatment with a suitable α-Amino-γ-butyrolactone furnished the desired SHLs in a modest to excellent yield (15-95%) (FIG. 3A). In order to determine the conformational preferences of the SHLs, a two-dimensional NOESY experiment was carried out on compound 4. There are clearly four conformations that compound 4 can adopt and based on the nuclear Overhauser effects (NOEs) it became evident that compound 4 prefers an E:Z ratio of 1:2 about the $sp^2$ amide-like.

Biofilm Inhibition Studies

A primary objective was to test the ability of SHLs to inhibit biofilm formation against *E. coli* RP437. All the SHLs exhibited an inhibitory activity towards the biofilm formation of *E. coli* RP437 (9-57%). Viable controls were required that would allow us to measure and compare the activity of SHLs against known biofilm inhibitors and naturally occurring AI-1 signal molecules. To serve this purpose, we resorted to the use of a brominated furanone (BF8 48) that has been known to exhibit strong biofilm inhibition in this strain of bacteria. Further, we were interested in evaluating the effect of naturally occurring AI-1 signal molecules on this strain of *E. coli*, although we note that *E. coli* does not contain the machinery to fabricate the AI-1 signals but has receptor proteins for binding AI-1 signals in its system that allow it to perceive other microbial cells in its vicinity. All of the SHLs in the library demonstrated maximum inhibitory effects on the biofilm formation at 200 μM (see FIG. 4 and FIG. 11). Our long term interest lies in developing biofilm inhibitors that are active at concentrations below 200 μM and hence this was our desired upper limit for screening. Among all the SHLs screened the most potent activity was displayed by vinyl-SHL 3, tolyl-SHL 11, and thienyl-SHL 12 (55-60%). The activity of this class of molecule is presumably similar or even marginally higher than that of brominated furanone (BF8 48) (56%). Moderate inhibition of biofilm formation is seen with butyl-SHL 8 (48%), hexyl-SHL 9 (42%), phenyl-SHL 10 (44%) and butoxy-SCPA 46 (42%). Other SHLs including vinyl-L-SHL 4, methyl-SHL 6, ethyl-SHL 7, and butoxy-SHL 1, as well as PSQ 45, and vinyl-SB 43 display weaker biofilm inhibition. Poor biofilm inhibition is seen with allyl-SHL2, vinyl-SCPA 47, IPSQ 42 and BSQ 44. With regards to the natural autoinducer molecules, none of the molecules tested displayed any affect on the biofilm formation.

For the present invention, the *E. coli* RP437 biofilms were allowed to develop in a 96-well plate in the absence or presence of SHLs. After 24 hours, the planktonic bacteria and remaining media were removed and the crystal violet was introduced in the wells. The bacterial biofilm being formed at the air/liquid interface on the inside wall of the well is stained readily by crystal violet. After removing the excess crystal violet and repeatedly washing the wells with water, followed by ethanol solubilization of the dye, allows quantification of the amount of biofilm by spectrophotometry ($OD_{600}$). The amount of DMSO used to dissolve the synthetic SHLs, BF8 and natural auto-inducers for inhibitor screening did not exceed 2% by volume. We note that DMSO (up to 3% by volume) does not attenuate the bacteria growth nor does it affect the biofilm formation (data not shown) of *E. coli* RP437. We believe that the observed biofilm inhibition activity cannot be directly attributed to any predominant structural feature inherent in the SHLs. Rather, the small deviations in the structures of the SHLs and their effect on biofilm formation could be a result of the nature of non-covalent forces that arise during SHLs presumed binding within the receptor active site.

Effect of SHLs on the Growth of *E. coli*

The toxicity of the SHLs and BF8 at a range of concentrations (1, 10, 25, 50, 100, 200 and 300 μM) was evaluated against *E. coli* RP437 to determine whether these small molecules elicit their inhibition effect through a toxic mechanism. The most potent SHLs including vinyl-SHL 3, methyl-SHL 6, ethyl-SHL 7, n-butyl-SHL 8, n-hexyl-SHL 9, phenyl-SHL 10, tolyl-SHL 11, thienyl-SHL 12 and butoxy-SCPA 46 were added in various concentrations to a 96-well plate containing *E. coli* RP437 in 200 μL LB (Luria-Bertani) media and their toxicity studied by monitoring the optical density at 600 nm ($OD_{600}$) of *E. coli* cultures after 0, 2, 4, 6, 8, 12 and 24 h. The effect induced by SHLs at 200 μM, the inhibitory concentration at which maximum biofilm inhibition occurs was interesting to observe. Growth studies reveal that all of the three potent SHLs exhibited poor or no growth inhibition (see FIGS. 5, 6 and 10). Vinyl-SHL 3 at 200 μM initially displays poor toxicity and at 4 h *E. coli* growth occurs to maximum of 77% relative to untreated sample. But, after 8 h, *E. coli* RP437 growth reverts back normally and exhibits growth values closer to the untreated sample (see FIG. 6). On the other hand, all the other SHLs tested 6-12 and butoxy-SCPA 46 show no inhibition of *E. coli* growth up to 300 μM.

The toxicity profile of BF8 48 would in turn allow a comparison to the library of SHLs. Parallel growth studies using BF8 48 and vinyl-SHL 3 treated and untreated control cultures in 96-well plates were performed. Inhibitor concentrations used during growth studies ranged from 100-300 μM. At each of these concentrations, cultures with BF8 48 indicated a marked attenuation of *E. coli* growth, indicating BF8 48 is toxic to *E. coli* RP437. Interestingly, cultures treated with vinyl-SHL 3 exhibited less toxicity compared to BF8 48 (see FIG. 6) and the bacterial cell densities remained unchanged over a period of 24 h. Surprisingly, the toxicity profile of vinyl-SHL 3 was the same at all the three concentrations tested (100, 200 and 300 μM). These studies have clearly indicated that vinyl-SHL 3 and other SHLs are well poised to become effective agents to control biofilm formation.

Ability of SHLs to Disperse Established Biofilm in *Escherichia coli*

Apart from the design and development of molecules that display bacterial biofilm inhibition, perhaps the greater challenge is to construct small molecules that will effectively disperse established biofilm. Generally, treatment of chronic microbial infections is commonly hindered by the presence of established biofilms that offer increased resistance to the entry of antibiotics and prevent their mode of action. In fact, bacteria in the biofilms are known to be greater than 1000-fold resistant to microbicides. More often than not, clinically, a physician has to often deal with established biofilm-based infection, hence, molecules that not only inhibit biofilm but also have capacity to effectively disperse biofilms are of great interest. *E. coli* RP437 strain was allowed to form biofilms over 24 h in the absence of any inhibitor. At the end of the 24 h, the media and the planktonic bacteria were removed, fresh media was added, and the remaining biofilm treated with BF8 48 and SHLs and further incubated for another 24 h. As biofilm inhibitory abilities of SHLs at 200 µM concentrations and below were tested, the dispersal abilities of various SHLs and BF were screened at 200 µM. Interestingly, BF8 48 displayed the most biofilm dispersal ability (39%) among all the molecules tested. In addition, the SHLs display a greater breadth in their ability to disperse biofilm (1-28%) with a quarter of biofilm being dispersed readily by vinyl-SHL 3 and vinyl-SCPA 47 (FIG. 6A and FIG. 7). Overall, the SHLs ability to disperse biofilm along with their relatively poor toxicity and biofilm inhibition ability makes them superior candidates to be used as a cocktail with established antibiotics to treat persistent infections.

Confocal Microscopy Analysis of *E. coli* Biofilms

The effects of SHLs upon the bacterial biofilm were examined; more specifically, the effect of SHLs upon the biofilm architecture. The biofilm inhibition and biofilm dispersal studies as enumerated in the previous sections demonstrated the ability of SHLs to significantly reduce biofilm formed by *E. coli* RP437. These studies were conducted by static biofilm assays employing crystal violet staining that indicates the total biomass that resides within a biofilm but provides no indication regarding the topology of the biofilms. To elucidate the topological features assumed by the *E. coli* RP437 biofilm in the presence of SHLs and BF8 48, studies of biofilms consisting of DsRed-express-labeled *E. coli* RP437 that is fluorescent and can be easily visualized by confocal laser scanning microscopy (CLSM) were performed. The confocal Z-stacked images revealing the depth of the confocal cut (every 1 µm) confirmed that BF8 48 and vinyl-SHL 3 inhibit the biofilm formation of *E. coli* RP437. Further, the stacked images in vinyl-SHL 3 indicating the maximum thickness of the biofilm is considerably smaller than the biofilms in BF8 48 and the untreated *E. coli* samples. We developed the biofilms consisting of DsRed-express-labeled *E. coli* on stainless steel coupons (316 L, 1 in×1 in.) for 24 h at 37° C. that were treated with BF8 48 or SHLs or were left untreated. All the samples were analyzed with CLSM (see FIG. 8) and the maximum thickness of biofilms calculated using the COMSTAT software. The maximum thickness of biofilm measurements revealed that vinyl-SHL 3 is able to reduce the thickness of the biofilm by ~52%; whereas, the BF8 48 surprisingly shows only 17% reduction in biofilm thickness (see FIG. 9). Moreover, butyl-SHL 8 and butoxy-SCPA 46 reduce the biofilm thickness by 38% and 27%, respectively. Overall, results indicate that vinyl-SHL 3 is a good inhibitor of biofilm formations and these results validate the biomass measurements done using the crystal violet test.

Effect of SHLs on the growth of *P. aeruginosa* PAO1

The toxicity of the SHLs 6-12 and BF4 at a 300 µM was evaluated against *P. aeruginoas* PAO1 to determine whether these small molecules inhibit the growth of PAO1 (see FIG. 12). All the SHLs tested have very little to no effect on the growth of PAO1. On the contrary, a known biofilm inhibitor, BF4, inhibited the growth of PAO1 almost completely at this concentration.

Confocal Microscopy Analysis of *P. aeruginosa* Biofilms

We developed the biofilms consisting of CFP-express-labeled *P. aeruginosa* on stainless steel coupons (316 L, ⅜ in×⅜ in.) for 24 h at 37° C. in the absence or presence of 400 µM hexyl-SHL 9, tolyl-SHL 11, thienyl-SHL 12, and BF4 49. All the samples were analyzed with CLSM (see FIG. 13) and the biomass, surface area, and mean thickness of biofilms were calculated using the COMSTAT software. Tolyl-SHL 11 reduced the biomass by ~90%, similar to that of the toxic BF4 49. Hexyl-SHL 9 and thienyl-SHL 12 showed mild and moderate biofilm inhibition, respectively (see FIG. 14).

Cytotoxicity Studies on Human Neuroblastoma Cancer Cells

After examining the efficacy of SHLs at inhibiting biofilm, dispersing established biofilms, and reducing the maximum thickness of biofilms without being toxic to the planktonic bacterial cells, we tested the cytotoxicity of the key potent SHLs on the human neuroblastoma cancer cell line SK-N-SH. These studies were conducted such that the SK-N-SH cells were subjected to the maximum concentrations of the key potent SHLs tested on bacteria. From these results it is obvious that most of the SHLs are toxic to human cells (see FIG. 15). Interestingly, butyl-SHL does not appear to be toxic even at the maximum concentration tested (300 µM). Since the other three molecules tested (vinyl-SHL 3, butoxy-SCPA 46 and vinyl-L-SHL 4) contain reactive side-chains and butyl-SHL 8 does not, the toxicity towards human neuroblastoma cancer cells may be the direct result of chemical interactions involving these reactive side-chains.

SHLs Mode of Action

The mechanism of action of these SHLs need to be elucidated their ability to inhibit and disperse bacterial biofilm formation should be probed. Along these lines, vinyl-SB 43 and vinyl-SHL 3 were treated with cysteine separately in DMSO ($d_6$). Cysteine was selected because it is one of the most biologically relevant amino acid residues that is ubiquitously found and exhibits high reactivity in physiological conditions. Moreover, cysteine residue has been found to exist in the active site of AHL receptors; close to the hydrophobic pocket in which the non-polar end group of the AHLs reside. Initial reactions revealed that vinyl-SB 43 is able to react rapidly with cysteine within 0.5 h, whereas, the vinyl-SHL 3 does not exhibit any reactivity at all. The first observation is consistent with the knowledge that vinyl-SB 43 is a better Michael acceptor and a more activated ester. The exocyclic double bond in vinyl-SB 43 experiences greater inductive effect due to the electronegativity of the carbonyl oxygen's, hence increasing the propensity of the exocyclic double bond to conjugate within the four-membered ring and that ultimately enhances the reactivity of the exocyclic double bond. But, on the other hand, vinyl-SHL 3 has an amide like functionality wherein the nitrogen creates a partial double bond character by conjugation with the endocyclic double bond which in turn reduces the reactivity of the vinyl group. If covalent immobilization is the only preferred mode of action of SHLs with reactive residues in the active site of SdiA, the nature of SHLs structure must dictate their reactivity and ability to inhibit biofilm formation. Instead, the presumably more reactive vinyl-SB 43 was observed inducing a mere 45% (26/57×100) of the maximum biofilm inhibition that is exerted by vinyl-SHL 3 (FIG. 9). This seeming lack of correlation that is observed between SHL structure and its chemical reactivity causing biofilm inhibition could perhaps be explained by considering a mechanism that takes into account not only a covalent immobilization but also the effect of non-covalent forces including hydrogen bonding that is exerted by the SHLs during their putative interaction with the cognate protein receptor.

The present invention thus encompassed successful synthesis of a library of squarate-based mimics of AI-1 quorum sensing signals, squarylated homoserine lactones (SHLs), with a rapid two-step synthesis. The SHLs are highly effective biofilm inhibitors against *E. coli* RP437. Among all of compounds in the SHL library, vinyl-SHL 3 displays the greatest inhibition of biofilm and it is even marginally superior to the known potent brominated furanone (BF8 48). In addition to biofilm inhibition, BF8 48 and SHLs seem to be able to disperse established *E. coli* biofilm. Moreover, growth studies reveal that the SHLs are generally non-toxic against the planktonic form of *E. coli*. However, when tested on human neuroblastoma cancer cells (SK-N-SH) the key potent SHLs are generally toxic with the exception of butyl-SHL. Because butyl-SHL 8 does not contain a reactive side chain, the chemical reactivity of the other SHLs tested (vinyl-SHL 3, vinyl-L-SHL 4 and butoxy-SCPA 46) may cause toxicity in human cells. Interestingly, the chemical reactivity of the SHLs does not appear to correlate with inhibition activity for biofilm formation by *E. coli* RP437. Also, not surprisingly, the natural AHL molecules do not promote *E. coli* biofilm formation. Biofilm studies with confocal microscopy validate the observed extensive biofilm inhibition by use of vinyl-SHL 3 during static biofilm assays. Greater than 50% reduction in the maximum thickness of biofilm occurs by use of vinyl-SHL 3. The well studied AI-2 or yet an unclear AI-3 pathway is thought to play a dominant role in the QS process in *E. coli*. The AI-1 pathway on the other hand constitutes a secondary mechanism as the *E. coli* has no known AHL synthase but only has a cognate receptor binding protein to recognize AHLs in other species. These results are quite promising in this context as the present invention can inhibit and disperse biofilms by use of micromolar concentrations of non-native ligands by targeting a secondary communication network. Furthermore, in *E. coli* there was no apparent QS modulation with respect to biofilm growth in the presence of natural auto-inducer molecules. But the presence of SHLs induced an inhibition of biofilm suggesting that these molecules can act as universal signal molecules and can be applied in other systems. Based on the present invention in combination with *E. coli*, these molecules behave as biofilm inhibitors. The efficacy of SHLs as biofilm inhibitors would be significant in a system like *Pseudomonas aeruginosa* wherein the AI-1 communication is the primary mechanism for QS. Future work should reveal the diverse applicability of the molecules of the present invention. Perhaps, it is necessary to remember, at this juncture that these molecules only represent the first generation of SHLs. Subsequent modifications in the SHLs would allow us to build a diverse and expansive set of signals that allow us to modulate QS and control bacterial biofilm, virulence and pathogenesis.

General Chemical Methods $^1$HNMR and $^{13}$C NMR spectra were recorded on a 300 and 500 MHz Bruker spectrometer and the chemical shifts were measured from the solvent peak as an internal standard (in CDCl$_3$, DMSO-d$_6$ and CH$_3$OD). Chemical shifts and Coupling Constants (J-value) are reported in ppm and Hertz respectively. The following abbreviations are used for spin multiplicity: s=singlet, d=doublet, t=triplet, q=quartet, m=multiplet, br=broad. High Resolution Mass spectra (HRMS) samples were analyzed by positive ion electrospray. Analytical thin-layer chromatography (TLC) was performed using EMD silica gel 60 F$_{254}$ pre-coated plates (0.25-mm thickness). Flash column chromatography was performed with Silica-P Flash Silica Gel (ultra pure 40-63 μm) from Silicycle Chemical Division (Quebec QC, Canada). Reagents and solvents used were commercial grades. Compounds 42, 44, 50-52 were purchased from Sigma-Aldrich and used directly. All reactions were carried out in oven-dried glassware under argon or nitrogen atmosphere unless otherwise specified.

Procedures

Synthesis of Butoxy-SHL (1)

To a solution of 3,4-dibutoxy-cyclobut-3-ene-1,2-dione (0.120 g, 0.53 mmol) in DMF at rt was added α-Amino-γ-butyrolactone-hydrochloride (0.070 g, 0.38 mmol) and triethylamine (1.5 equiv.) and the mixture refluxed overnight. The completion of the reaction was monitored by TLC for the disappearance of starting material. The reaction was quenched with water and extracted with EtOAc (3×100 mL). The organic layers were collected, washed with brine (2×25 mL), dried over Na$_2$SO$_4$ and concentrated in vacuo. Flash column chromatography (SiO$_2$, 100% EtOAc) yielded compound 1 as a brown solid.

1: Yield (28%), R$_f$=0.50 (100% EtOAc); $^1$H NMR (CDCl$_3$, 300 MHz) δ 9.05 (1 H, m), 4.99-4.23 (5 H, m), 4.39-4.24 (2 H, m), 2.62-2.53 (1 H, m), 2.32-2.18 (1H, m), 1.72-1.70 (1 H, m), 1.39-1.37 (1 H, m), 0.93-0.88 (3 H, m); $^{13}$C NMR (CDCl$_3$, 300 MHz) δ 189.5, 175.5, 173.2, 73.6, 66.2, 53.2, 52.9, 41.2, 40.9, 40.6, 40.4, 40.1, 39.8, 39.5, 32.3, 30.1, 29.8, 18.9, 14.4; HRMS Calcd. for C$_{12}$H$_{15}$NO$_5$ [M]Na$^+$276.0842. found 276.0839

Synthesis of Intermediates 53 and 54

To a solution of 3,4-dibutoxy-cyclobut-3-ene-1,2-dione (1 equiv.) in THF at −78° C. was added allyl or vinyl magnesium bromide (1 M, 1.35 equiv.) dropwise. The reaction mixture was stirred for 6-8 h and the reaction monitored by TLC for disappearance of starting material. The reaction was quenched with water and extracted with CH$_2$Cl$_2$ (3×100 mL). The organic layers were collected, washed with brine (25 mL), dried over Na$_2$SO$_4$ and concentrated in vacuo. Flash column chromatography (SiO$_2$, 15-20% EtOAc in Hexanes) yielded compounds 53 or 54.

53: Yield (73%), yellow oil, R$_f$=0.30 (20% EtOAc in Hexanes); $^1$H NMR (CDCl$_3$, 300 MHz) δ 5.72-5.60 (1 H, m), 5.09-5.0 (2 H, m), 4.39-4.24 (2 H, m), 4.17-4.11 (3 H, m), 2.61-2.46 (2 H, m), 1.72-1.62 (2 H, m), 1.58-1.49 (2 H, m), 1.43-1.18 (4 H, m), 0.91-0.73 (6H, m); $^{13}$C NMR (CDCl$_3$, 300 MHz) δ 187.5, 168.2, 133.0, 132.6, 199.2, 85.9, 73.4, 70.9, 37.9, 32.1, 31.8, 19.1, 18.9, 14.0, 13.9; HRMS calcd for C$_{15}$H$_{24}$O$_4$ [M]Na$^+$291.1567. found 291.1564

54: Yield (59%), red oil, R$_f$=0.30 (20% EtOAc in Hexanes); $^1$H NMR (CDCl$_3$, 300 MHz) δ 6.58-5.32 (3 H, m), 4.75-4.71 (1 H, t), 4.39-4.35 (1 H, t), 3.70-3.57 (2 H, m), 1.82-1.19 (9 H, m), 0.94-0.82 (6 H, m); $^{13}$C NMR (CDCl$_3$, 300 MHz) δ 194.9, 193.4, 190.7, 180.9, 173.7, 128.9, 127.4, 122.7, 122.22, 122.2, 113.3, 77.9, 77.5, 77.1, 75.3, 73.8, 66.0, 62.9, 32.2, 32.1, 31.63, 19.5, 19.2, 19.1, 18.8, 14.2, 13.94, 13.9; HRMS Calcd. for C$_{14}$H$_{22}$O$_4$ [M]Na$^+$277.1413. found 277.1410

Representative Procedure for the Synthesis of Allyl-SHL (2), Vinyl-SHL (3), Vinyl-L-SHL (4), Butyl-SHL (8) or Vinyl-D-SHL (5)

To a solution of α-Amino-γ-butyrolactone (1 equiv.) was added DIPEA (1 equiv.) at 0° C. and the mixture was stirred for five minutes. To this solution, 42, 56 or 57 (1 equiv.) in CH$_2$Cl$_2$ was introduced by dropwise addition, respectively.

The reaction mixture was stirred for 8 h and the completion of the reaction monitored by TLC for the disappearance of starting material. The reaction was quenched with water and extracted with $CH_2Cl_2$ (3×100 mL). The organic layers were collected, washed with brine (25 mL), dried over $Na_2SO_4$ and concentrated in vacuo. Flash column chromatography ($SiO_2$, 80% EtOAc in Hexanes→100% EtOAc) yielded the targeted compounds.

Compound 2:

Yield (57%), red powder, $R_f$=0.50 (100% EtOAc); $^1H$ NMR ($CDCl_3$, 300 MHz) δ 9.37-9.23 (1 H, m), 7.06-6.43 (2 H, m), 5.09-4.81 (1 H, m), 4.46-4.27 (2 H, m), 2.76-2.61 (1 H, m), 2.45-2.41 (1 H, m), 1.94-1.90 (3 H, m); $^{13}C$ NMR ($CDCl_3$, 300 MHz) δ 192.7, 190.4, 189.9, 179.9, 179.4, 175.5, 165.0, 163.9, 139.7, 139.4, 139.0, 121.4, 119.8, 66.5, 66.3, 53.6, 53.4, 53.3, 41.2, 40.9, 40.6, 40.3, 40.0, 39.7, 39.5, 30.3, 29.2, 20.4, 20.2, 18.6; HRMS Calcd. for $C_{11}H_{11}NO_4$ [M]+$Na^+$244.0580. found 244.0575.

Compound 3:

Yield (49%), yellow powder, $R_f$=0.50 (100% EtOAc); $^1H$ NMR ($CDCl_3$, 300 MHz) δ 9.61-9.42 (1 H, m), 6.88-6.67 (1 H, m), 6.23-6.44 (1 H, m), 5.75-5.63 (1 H, m), 5.10-4.70 (1 H, m), 4.45-4.25 (2 H, m), 3.31-2.60 (1 H, m), 2.48-2.24 (1 H, m); $^{13}C$ NMR ($CDCl_3$, 300 MHz) δ 180.6, 175.4, 163.9, 126.4, 125.2, 124.7, 124.5, 66.5, 66.4, 53.7, 53.4, 41.2, 40.9, 40.7, 40.4, 40.1, 39.8, 39.5, 30.3, 29.2; HRMS Calcd. for $C_{10}H_9NO_4$ [M]+$Na^+$230.0424. found 230.0422.

Compound 4:

Yield (35%), yellow oil, $R_f$=0.50 (100% EtOAc); $^1H$NMR ($d_6$-DMSO, 300 MHz): δ 9.46-9.43 (1 H, dd), 6.92-6.68 (1 H, 2 dd), 6.45-6.24 (1 H, 2 dd), 5.76-5.65 (1 H, 2 dd), 5.11-5.07 (1 H, 2 m) 4.46-4.28 (2 H, t and m), 2.66-2.63 and 2.36-2.26 (2 H, 2 m). $^{13}C$NMR ($d_6$-DMSO, 300 MHz): δ 175.4, 163.8, 126.4, 125.2, 124.7, 66.5, 53.7, 53.4, 30.3, 29.1. HRMS: Calcd. for $C_{10}H_9NO_4$ [M]+ $Na^+$230.0427, found 230.0424.

Compound 5:

Yield (15%), yellow oil, $R_f$=0.40 (100% EtOAc); $^1H$ NMR ($CDCl_3$, 300 MHz) δ 9.56-9.44 (1H, m), 6.95-6.25 (3H, m), 5.75-5.65 (1H, m), 5.14-4.79 (1H, m), 4.41-4.22 (2H, m), 2.43-2.23 (1H, m), 2.70-2.58 (1H, m); $^{13}C$ NMR ($CDCl_3$, 300 MHz) δ 193.8, 180.7, 180.3, 175.4, 163.9, 162.7, 126.4, 125.2, 124.7, 124.5, 66.5, 66.4, 53.7, 53.4, 41.2, 40.9, 40.7, 40.4, 40.1, 39.8, 39.6, 30.3, 29.2; HRMS Calcd. for $C_{10}H_9NO_4$ [M]+$Na^+$230.0424. found 230.0424.

Compound 6:

Yield (25%), yellow oil, $R_f$=0.20 (Hexane:Ethyl acetate, 4:1); $^1H$ NMR (300 MHz, $CDCl_3$): δ 4.44-4.28 (m, 2H), 4.23-4.18 (m, 2H), 3.22 (br s, 1H), 1.91-1.69 (m, 4H), 1.63-1.58 (m, 2H), 1.46-1.35 (m, 4H), 0.96-0.88 (m, 9H); HRMS: Cacld. for $MH^+$: 196.0609. found: 196.0598.

Compound 7:

Yield (88%), colorless oil, $R_f$=0.31 (100% EtOAc); $^1H$ NMR (300 MHz, $CDCl_3$): δ 7.54 (d, $J_{H-H}$=7.89 Hz, 1H), 5.13-5.03 (m, 1H), 4.49 (t, $J_{H-H}$=9.12 Hz, 1H), 4.37-4.10 (m, 1H), 2.84-2.75 (m. 1H), 2.61 (q, $J_{H-H}$=7.62 Hz, 2H), 2.50-2.43 (m, 1H). 1.25 (t, $J_{H-H}$=7.53 Hz, 3H); HRMS: Cacld. for $MH^+$: 210.0766. found: 210.0763.

Compound 8:

Yield (56%), light yellow oil, $R_f$=0.52 (100% EtOAc); $^1H$NMR ($d_6$-DMSO, 300 MHz): δ 5.05-4.98 (1 H, t), 4.45-4.28 (2 H, m), 2.65-2.61 and 2.31 (2 H, m), 2.56-2.48 (2 H, t), 1.63-1.52 (2 H, m), 1.36-1.29 (2 H, m), 0.91-0.84 (3 H, t). $^{13}C$NMR ($d_6$-DMSO, 300 MHz): δ 184.9, 66.2, 63.5, 53.1, 30.2, 29.4, 28.5, 26.2, 25.1, 23.0, 23.0. HRMS: Cacld. for $C_{12}H_{15}NO_4$ [M]+$Na^+$260.0893. found: 260.0893.

Compound 9:

Yield (60%), white solid, $R_f$=0.23 (Hexane:Ethyl acetate, 1:2); $^1H$ NMR (300 MHz, DMSO-d6): δ 7.11 (br, 1H). 5.00 (b, dd, J=20.4, 7.8 Hz. 1H). 4.42 (t, 1H. J=7.8 Hz), 4.28 (m. 1H), 2.68 (m, 1H), 2.54 (t, 2H, J=7.5 Hz), 2.34 (m, 1H), 1.62 (m, 2H), 1.32 (m, 6H), 0.91 (t, 3H, J=7.2 Hz); $^{13}C$ NMR (75 MHz, DMSO-d6): δ 195.2, 193.0, 186.0, 175.9, 175.8, 66.8, 53.9, 32.5, 30.9, 30.3, 27.0, 25.9, 23.6, 14.7; HRMS: Cacld. for $M^+$: 265.2309. found: 265.1310.

Compound 10:

Yield (65%), white solid, $^1H$ NMR (300 MHz, DMSO-d6): δ 9.31 (d, 1H, J=6 Hz), 7.91 (d, 1H, J=9 Hz), 7.57 (d-d, 1H, J=12 Hz), 5.30 (q, 1H, J=18 Hz), 4.49 (t, 1H, J=9 Hz), 4.35 (m, 1H), 2.80 (m, 1H), 2.55 (m, 1H); $^{13}C$ NMR (75 MHz, DMSO-d6): δ 193.4, 189.6, 180.0, 175.5, 163.5, 131.8, 130.0, 129.6, 127.1, 66.4, 53.7, 29.9. HRMS: Cacld. for [M]+$Na^+$: 280.2312. found: 280.0578.

Compound 11:

Yield (95%), pale yellow solid, $R_f$=0.55 (Hexane:Ethyl acetate, 1:4); $^1H$ NMR (300 MHz, DMSO-$d_6$): δ 9.28 (br s, 1H), 7.89 (d, $J_{H-H}$=7.95 Hz, 2H), 7.39 (d, $J_{H-H}$=7.86 Hz, 2H), 5.33-5.26 (m, 1H), 4.49-4.30 (m, 2H), 2.71-2.63 (m, 1H), 2.43 (br s, 1H), 2.38 (s, 3H). $^{13}C$ NMR (75 MHz, DMSO-$d_6$): δ 192.3, 188.9, 178.9, 174.7, 162.98, 141.4, 129.8, 126.3, 126.2, 65.5, 52.8, 29.2, 21.3. HRMS. found 271.0836 [$M^+$], Calcd. for $M^+$271.0839.

Compound 12:

Yield (60%), pale yellow solid. $R_f$=0.25 (Hexane:Ethyl acetate, 1:2); $^1H$ NMR (300 MHz, DMSO-d6): δ 9.35 (d, 1H, J=4.5 Hz), 8.04 (d. 1H. J=4.8 Hz), 7.87 (d, 1H, J=3.6 Hz), 7.39 (t, 1H, J=4.2 Hz), 5.27 (m, 1H), 4.48 (t, 1H, J=8.9 Hz), 4.32 (m 1H), 2.29 (m, 1H), 2.41 (m, 1H); $^{13}C$ NMR (75 MHz, DMSO-d6): δ 190.3, 186.6, 176.8, 174.6, 157.7, 132.2. 128.8, 128.8, 128.7, 65.6, 52.9, 29.3; HRMS: Cacld. for $M^+$: 263.0247. found: 263.0240.

Representative Procedure for the Synthesis of Butoxy-SCPA (46) or Vinyl-SCPA (47)

To a solution of 3,4-dibutoxy-cyclobut-3-ene-1,2-dione or 7 (1 equiv.) in $CH_2Cl_2$ at rt was added cyclopentylamine (1 equiv.) dropwise and the reaction mixture was stirred for 4 h. The completion of the reaction was monitored by TLC for the disappearance of starting material. The reaction was quenched with water and extracted with $CH_2Cl_2$ (3×100 mL). The organic layers were collected, washed with brine (25 mL), dried over $Na_2SO_4$ and concentrated in vacuo. Flash column chromatography ($SiO_2$, 25% EtOAc in Hexanes) yielded compound 46 or 47 as colorless oil.

Compound 46: $R_f$=0.35 (25% EtOAc in Hexanes); $^1H$ NMR ($CDCl_3$, 300 MHz) δ 8.86-8.62 (1 H, m), 4.65-4.59 (4 H, m), 4.34-3.93 (1 H, m), 1.86-1.22 (10 H, m), 0.93-0.86 (3 H, m); $^{13}C$ NMR ($CDCl_3$, 300 MHz) δ 196.6, 173.5, 73.1, 56.57, 56.3, 41.2, 40.9, 39.8, 39.5, 34.1, 33.9, 32.4, 24.2, 24.1, 19.0, 18.9, 17.5, 14.4; HRMS Calcd. for $C_{13}H_{19}NO_3$ [M]+$Na^+$ 260.1257. found 260.1258.

Compound 47: $R_f$=0.30 (25% EtOAc in Hexanes); $^1H$ NMR ($CDCl_3$, 300 MHz) δ 9.35-9.05 (1 H, m), 6.85-5.61 (3 H, m), 4.63-3.90 (2 H, m), 1.93-1.22 (5 H, m), 0.93-0.84 (2 H, m); $^{13}C$ NMR ($CDCl_3$, 300 MHz) δ 179.3, 176.1, 126.4, 125.1, 123.9, 123.8, 74.9, 73.4, 56.7, 41.2, 40.9, 40.6, 40.3, 40.1, 39.8, 39.5, 34.1, 33.4, 24.4, 24.2; HRMS Calcd. for $C_{11}H_{13}NO_2$ [M]+$Na^+$214.0839. found 214.0841.

Compound Handling

The stock solutions of all the synthetic compounds (0.1, 1.0 and 10 mM) were prepared in DMSO and stored at −20° C. in argon purged sealed vials. The total amount of DMSO used in small molecule screens did not exceed 2% (by volume). Even after ~4 months, $^1$H NMR revealed no visible deterioration in SHLs (solubilized in DMSO).

Bacteriology

All the biological reagents were purchased from Sigma-Aldrich and Fisher Scientific and used according to enclosed protocols. For the purpose of biofilm formation, in our studies, we used *E. coli* RP437 strain. In order to visualize the bacterial cells during confocal studies, the DsRed-Express fluorescent protein was expressed in *E. coli* RP437 by transformation of the plasmid pRSH103, obtained from pDsRed-Express (BD, Franklin Lakes, N.J.) by replacing the ampicillin resistant marker with the tetracycline (Tet) resistant marker tet$^R$. To maintain the plasmid pRSH103, a concentration of 3 mg/mL tetracycline was added at to all the developing cultures. *E. coli* RP437 was incubated in LB medium (Luria-Bertani) containing 10 g/L tryptone, 5 g/L yeast extract, and 10 g/L sodium chloride at pH 7.04 and grown at 37° C. using a standard laboratory incubator with shaking (200 rpm). Solvent resistant polypropylene or polystyrene 96-well microtiter plates with flat-shaped bottom were used for all inhibition and dispersion assays. All optical density measurements were obtained with Biotek ELx800 (BioTek instruments, Inc, Winooski, Vt., USA) absorbance plate reader using Gen5™ data analysis software.

Static Biofilm Inhibition Assay

An overnight culture of *E. coli* RP437 grown in LB media ($OD_{600}$ of 1.0) containing streptomycin (10 µg/mL) was subsequently sub-cultured to an $OD_{600}$ of 0.04 (1:100 dilution with LB media). To each well in the solvent resistant polypropylene or polystyrene-based 96-well microtiter plates were added 200 µL of the sub-cultured bacteria respectively. To each of the wells containing the bacterial cultures varying concentrations of the synthetic molecules was added and the contents in each well were gently mixed. Control wells comprised of untreated bacterial culture (four replicates) and the LB media (four replicates). The microtiter plates were then covered and wrapped in a Saran wrap and allowed to incubate at 37° C. for 24 hours without shaking. After that time, the microbial medium in each well was discarded and the remaining biofilm that was formed during incubation was stained with 225 µL of a 0.1% crystal violet solution and allowed to incubate at room temperature for 30 minutes. After the incubation period, the crystal violet was discarded and the wells were gently washed twice with water (230-250 µL) and allowed to air dry for 15-20 minutes. For the purpose of solubilizing the remaining crystal violet that had stained the biofilm present in the interior of the 96-well plates, a 250 µL solution of 95% ethanol was used. After the addition of 95% ethanol, the contents of each well were mixed thoroughly and allowed to sit for 15-20 minutes. Finally, the biofilm formed was quantified by transferring 100 µL of the ethanol solution into a fresh polystyrene microtiter dish that was subsequently read by an absorbance plate reader ($A_{600}$). After elimination of background absorbance, the percentage inhibition was calculated by dividing the amount of absorbed crystal violet in wells that contained the synthetic compound by the amount of absorbed crystal violet in wells that contained bacteria only (control). Biofilm assays for each synthetic compound were repeated two to three times and each concentration considered for inhibition studies were tested over four replicates.

Growth Studies

An overnight culture of *E. coli* RP437 grown in LB media ($OD_{600}$ of 1.0) containing streptomycin (10 µg/mL) was subsequently sub-cultured to an $OD_{600}$ of 0.04 (1:100 dilution with LB media). To each well in the solvent resistant polypropylene or polystyrene-based 96-well microtiter plates were added varying concentrations of the synthetic molecules respectively (1, 10, 25, 50, 100, 200 and 300 µM). Further, to each of the wells containing the known concentrations of synthetic molecules was added 200 µL of the sub-cultured bacteria and the contents in each well were gently mixed. Control wells comprised of untreated bacterial culture (four replicates) and the LB media (four replicates). The microtiter plates were then covered and allowed to incubate at 37° C. for 24 hours with shaking at 200 rpm. The $OD_{600}$ values in each well was measured at 0, 2, 4, 6, 8, 12, 24 h after inoculation using Biotek ELx800 absorbance plate reader using Gen5™ data analysis software. For each synthetic compound, the growth experiments were repeated twice and each of the concentrations was tested over four replicates.

Static Biofilm Dispersion Assay

An overnight culture of *E. coli* RP437 grown in LB media ($OD_{600}$ of 1.0) containing streptomycin (10 µg/mL) was subsequently sub-cultured to an $OD_{600}$ of 0.03-0.04 (1:100 dilution with LB media). To each well in the solvent resistant polypropylene or polystyrene-based 96-well microtiter plates were added 200 µL aliquots of the microbial sub-culture. The control wells comprised of untreated bacterial culture (four replicates) and the LB media (four replicates). The microtiter plates were then covered and wrapped in a Saran wrap and allowed to incubate at 37° C. for 24 hours without shaking to allow formation of biofilm. After that time, the microbial medium in each well was discarded, leaving only the pre-formed biofilm on the inside of the polystyrene wells and fresh LB media (200 µL) was introduced. At this juncture LB alone was added to generate a control row and predetermined concentrations of the compound of interest were introduced. Again, the plates were wrapped in Saran wrap and allowed to incubate at 37° C. for 24 hours after which the microbial medium in each well was discarded and the remaining biofilm was stained with 225 µL of a 0.1% crystal violet solution and allowed to incubate at room temperature for 30 minutes. After the incubation period, the crystal violet was discarded and the wells were gently washed twice with water (240 µL) and allowed to air dry for 15-20 minutes. For the purpose of solubilizing the remaining crystal violet that had stained the biofilm present in the interior of the 96-well plates, a 250 µL solution of 95% ethanol was used. After the addition of 95% ethanol, the contents of each well were mixed thoroughly and allowed to sit for 15-20 minutes. Finally, the biofilm formed was quantified by transferring 100 µL of the ethanol solution into a fresh polystyrene microtiter dish that was subsequently read by an absorbance plate reader ($A_{600}$). After elimination of background absorbance, the percentage dispersion was calculated by dividing the amount of absorbed crystal violet in wells that contained the synthetic compound by the amount of absorbed crystal violet in wells that contained bacteria only (control). Biofilm assays for each synthetic compound were repeated two times and each concentration considered for inhibition studies were tested over four-to-eight replicates.

Confocal Imaging of Biofilms

An overnight culture of *E. coli* RP437 pRSH103 grown in LB media ($OD_{600}$ of 1.0) containing tetracycline (3 µg/mL) was subsequently sub-cultured to an $OD_{600}$ of 0.04 (1:100 dilution with LB media). To each well in the solvent resistant polypropylene or polystyrene-based 24-well microtiter plates was added 200 µM synthetic molecules in DMSO solution respectively. In addition, to each of the wells containing the known concentrations of synthetic molecules was added 2 mL of the sub-cultured bacteria and the contents in each well were gently mixed. The control wells comprised of untreated bacterial culture (four replicates) and the LB media (four replicates). Stainless steel coupons (ca. 1 cm×1 cm) were introduced in each of the desired wells respectively. The microtiter plates were then covered and wrapped in a Saran wrap and allowed to incubate at 37° C. for 24 hours without shaking. Each of the coupons containing the biofilm was washed gently by dipping the surfaces vertically in a 0.85% NaCl buffer three times (fresh buffer used for each dipping step). The *E. coli* biofilms expresses DsRed-Express constitutively and were visualized using confocal laser scanning microscopy (CLSM) by excitation with a HeNe laser at 543 nm. The fluorescent emission was detected with a LP 560 nm emission filter. The coupons were gently placed upside down on a microscope cover glass (24×60 mm, No. 2, VWR International LLC, West Chester, Pa., USA) and analyzed with CLSM. We obtained a series of images (20-60) for each position on the coupon at 1 μm intervals in Z-section for a three-dimensional view of the biofilm (from the substratum to the top of biofilm). The COMSTAT software written on the Matlab platform[106] was used to determine the maximum thickness (μm) of the biofilms. Overall, the confocal Z-stack analyses were performed on 4-6 positions on each coupon, and the experiment was repeated twice each with four replicates.

Human Neuroblastoma Cancer Cell Cytotoxicity Assay

A previously grown T-flask of SK-N-SH cells was observed under a microscope to confirm the confluence of the cells. Next, the old media was discarded and the adherent cells were washed with ~10 mL of MEM(−). The wash was discarded and 2 mL of Trypsin-EDTA solution was added to the T-flask and incubated for 10 minutes at 37° C. and at 5% atmosphere of $CO_2$. Afterwards, the flask was viewed under a microscope to determine if the cells were suspended in the solution. Subsequently, ~8 mL of MEM(+) was added to the flask and carefully mixed via pipette to break-up any large clusters of cells. 100 μL of the culture was added to an Eppendorf tube and combined with 100 μL of Trypsin Blue. A hemocytometer and glass cover slide was carefully cleaned with a kimwipe and ethanol. Placing the glass cover slide on top of the hemocytometer, 10 μL of the mixture in the Eppendorf tube was pipetted into the two grooves on the hemocytometer, avoiding the generation of bubbles. The hemocytometer was viewed one chamber at time under a microscope and the live cells were counted using the hemocytometer cell counting method. The remaining cell culture in the T-flask was diluted with MEM(+) to 25 mL such that there would be ~5000 cells/mL. 100 μL of the culture was placed into wells on a 96 well plate such that one column had only MEM(+) and the wells on the outer perimeter of the plate were left empty. Four plates were made in this manner so that there would be plates for times 0, 24, 48, and 72 h. The plate was then incubated for 24 h at 37° C. and at 5% atmosphere of $CO_2$. Subsequently, the old media was discarded and the wells were subjected to either 200 μM or 300 μM solutions of compounds 3, 4, 8, and 46 in MEM(+) (100 μL) such that one column still contained only MEM(+) and one column contained MEM(+) and untreated cells. The plate was incubated for 1 h and then the solutions were discarded and fresh MEM(+) media was added (100 μL). Each plate was then incubated for the desired time (0, 24, 48, or 72 h). After incubation, 10 μL of CCK-8 solution was added to each well and then the plate was incubated for 2 h followed by reading the $OD_{450}$ with a microplate reader.

Figure 2:
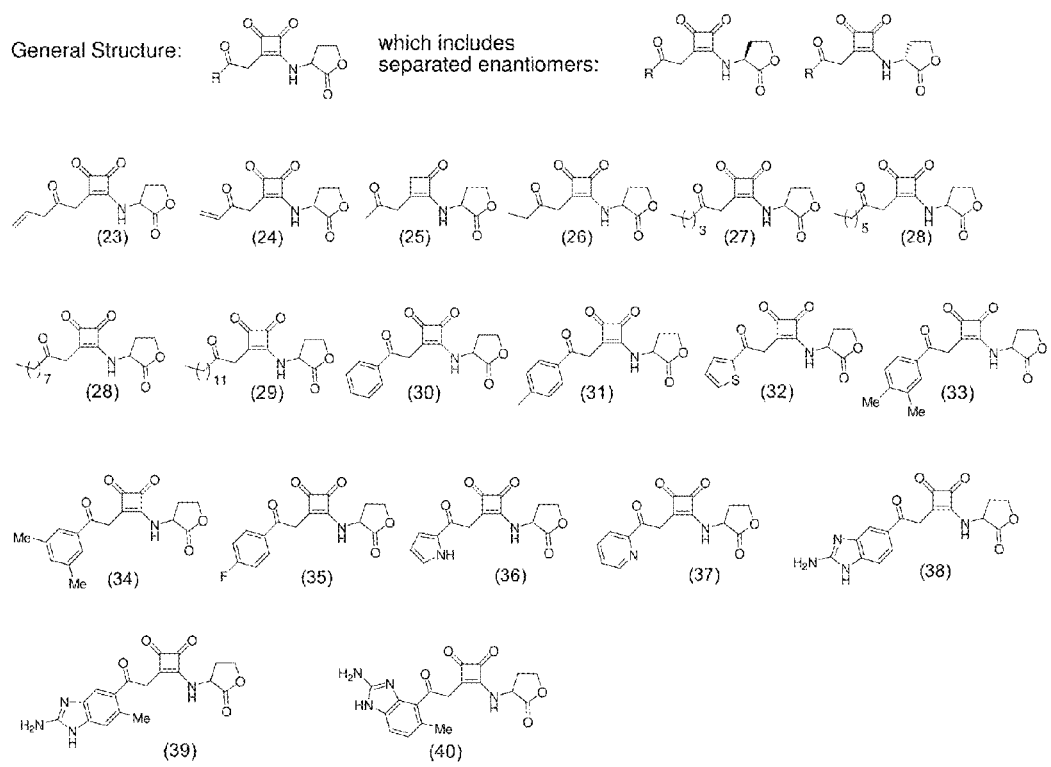
FIG. 2 is a general library of the second generation of squarylated homoserine lactones as synthetic mimics of autoinducer.

Referring to FIG. 1, the library of squarylated homoserine lactones discussed above includes additional compounds based the same general structure of _Generation 1_, including separate enantiomers. Similarly, as seen in FIG. 2, the library of squarylated homoserine lactones discussed above includes additional compounds based the same general structure of _Generation 2_, including separate enantiomers. Referring to FIG. 3, other relevant and background structures have been depicted.

What is claimed is:

1. A squarylated homoserine lactone, comprising the structure:

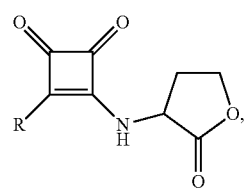

wherein R is a group selected from the group consisting of methyl, ethyl, n-butyl, n-hexyl, phenyl, tolyl, and thienyl.

2. The squarylated homoserine lactone of claim 1, wherein said squarylated homoserine lactone is characterized by an ability to modulate quorum sensing.

3. The squarylated homoserine lactone of claim 1, wherein said squarylated homoserine lactone is characterized by an ability to inhibit biofilms.

4. A squarylated homoserine lactone, wherein said structure is selected from the group consisting of

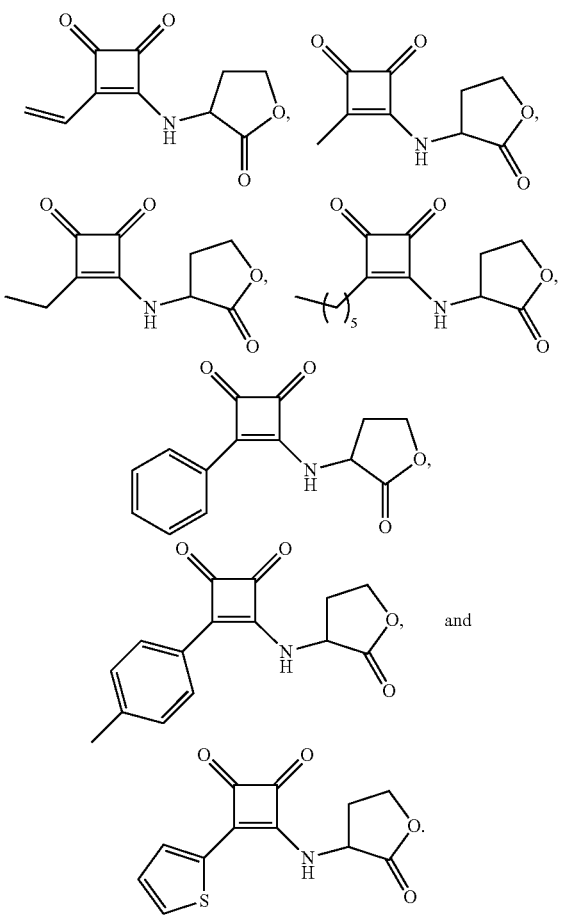

and

5. A squarylated homoserine lactone, comprising the structure:

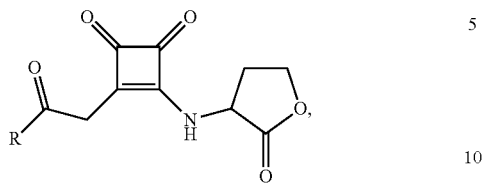

wherein R is a group selected from the group consisting of methyl, ethyl, n-butyl, n-hexyl, phenyl, tolyl, and thienyl.

6. The squarylated homoserine lactone of claim 5, wherein said squarylated homoserine lactone is characterized by an ability to modulate quorum sensing.

7. The squarylated homoserine lactone of claim 5, wherein said squarylated homoserine lactone is characterized by an ability to inhibit biofilms.

* * * * *